United States Patent [19]

Hirohara et al.

[11] 4,170,696

[45] Oct. 9, 1979

[54] ENZYME-IMMOBILIZATION CARRIER AND PREPARATION THEREOF

[75] Inventors: Hideo Hirohara; Shigeyasu Nabeshima, both of Ibaraki; Tsuneyuki Nagase, Takatsuki, all of Japan

[73] Assignee: Sumitomo Chemical Company, Limited, Osaka, Japan

[21] Appl. No.: 875,120

[22] Filed: Feb. 3, 1978

[30] Foreign Application Priority Data

Nov. 5, 1977 [JP] Japan .................. 52-132750

[51] Int. Cl.$^2$ ............................................. C08G 2/00
[52] U.S. Cl. ................................... 521/29; 521/32; 521/36; 521/53; 521/55; 435/180
[58] Field of Search ................... 260/2.5 R, 2.5 B; 521/29, 32, 36

[56] References Cited

U.S. PATENT DOCUMENTS

| | | | |
|---|---|---|---|
| 3,663,467 | 5/1972 | Albright | 260/2.5 B |
| 3,767,600 | 10/1973 | Albright | 260/2.5 B |
| 3,886,125 | 5/1975 | Chromecek | 260/2.5 R |
| 4,046,720 | 9/1977 | Rembaum et al. | 260/2.5 B |
| 4,070,348 | 1/1978 | Kraemes | 260/2.5 B |

*Primary Examiner*—Morton Foelak
*Attorney, Agent, or Firm*—Cushman, Darby & Cushman

[57] ABSTRACT

A diethylaminoethyl derivative or its salt is reacted with a synthetic resin of a macroporous type having functional groups reactive with said diethylaminoethyl derivative or its salt, having a specific area of at least 1 m$^2$/g-dry resin and containing macropores of which the total volume of those with pore sizes from 100 Å to 2,000 Å is at least 0.1 cc/g-dry resin, in the presence of an alkaline compound to give an enzyme-immobilization carrier which can provide an immobilized enzyme high in activity with good activity retentivity and also large in amount of the immobilized enzyme per unit weight of the carrier.

22 Claims, No Drawings

ENZYME-IMMOBILIZATION CARRIER AND PREPARATION THEREOF

This invention relates to an enzyme-immobilization carrier and a process for producing the same. More particularly, this invention pertains to an enzyme-immobilization carrier comprising a synthetic resin containing diethylaminoethyl groups obtained by reacting a diethylaminoethyl derivative or its salt with a macroporous synthetic resin (hereinafter sometimes referred to merely as "resin"; all of the resins herein mentioned refer to pure synthetic resins, excluding polysaccharide derivatives) having functional groups reactive with said diethylaminoethyl derivative or its salt in the presence of an alkaline compound, and also to a process for producing the same.

There have been developed in recent years enzyme immobilization techniques because of the usefulness of immobilized enzymes in commercial application (refer to, for example, C. R. Zaborsky, Immobilized Enzymes, C.R.C. Press, 1973) and therefore various immobilization carriers are known in the art. Among these carriers, polysaccharides and their derivatives, for example, crosslinked dextran, have been frequently used and they proved to be successful as carriers for several enzymes (Enzymologia, Vol. 31, p. 214, 1966). These polysaccharides, however, are insufficient in mechanical strength and therefore it is difficult to obtain a sufficient flow velocity in column operation. Further, they are liable to cause clogging during the operation and weak in resistance to microbial attack. Another great problem is that ionically bonded enzymes on these carriers are easily released when a large amount of electrolytes are present in a reaction mixture. On the other hand, in the late nineteen fifties, it had been known to use synthetic resins, especially ion-exchange resins as enzyme-immobilization carriers. But these resins have been evaluated to be of little practical value due to small quantity of enzymes carried per unit weight of carrier and low activity of the immobilized enzymes obtained. Ion-exchange resins having synthetic resin matrix, however, have several outstanding features superior to polysaccharides and their derivatives. They generally maintain sufficient mechanical strength and can be durable for continuous running for a long term in a large scale column without suffering from a great extent of damages. Further, they have a suitable particle size to ensure sufficient flow velocity in column operation and are strongly resistant to microbial attack.

Under the circumstances as mentioned above, the present inventors have made extensive studies and found that specifically modified ion-exchange resins in which diethylaminoethyl (hereinafter referred to as "DEAE") groups having specific affinity with a large number of enzyme proteins are introduced into synthetic resins having specific physical and chemical properties are excellent enzyme-immobilization carriers. The present invention has been accomplished, based on this finding.

The object of the present invention is to provide an enzyme-immobilization carrier which can give an immobilized enzyme having a high immobilized enzyme activity with excellent activity retentivity and/or containing a large quantity of immobilized enzymes per unit weight of the carrier and a method for producing the same. The other object of the present invention is to provide an enzyme-immobilization carrier suitable for commercial application which can stabilize enzymes by immobilization and enable repeated and continuous uses of enzymes which are in themselves catalysts for homogenous aqueous reactions, and a method for producing the same.

According to the present invention, there is provided an enzyme-immobilization carrier comprising a DEAE-modified resin obtained by reacting a diethylaminoethyl derivative of the formula

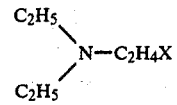

(wherein X is halogen or hydrogensulfate) or its acid addition salt, for example, β-diethylaminoethyl hydrogensulfate, β-diethylaminoethyl chloride hydrochloride, under alkaline conditions with a synthetic resin having functional groups reactive with said DEAE derivatives such as hydroxyl group, primary amino group, secondary amino group, imino group or sulfhydryl group, especially a macroporous resin having specific surface area of 1 $m^2/g$ or more and containing macropores with pore sizes of 100 Å to 2000 Å, the total volume of said macropores being at least 0.1 cc/g-dry resin. The DEAE-modified resin of the present invention is found to have not only the excellent characteristics of ion-exchange resins as mentioned above such as mechanical strength, column operability and resistance to microbial attack, but also it is an extremely excellent enzyme-immobilization carrier which can give an immobilized enzyme having a large quantity of immobilized enzymes, a high specific activity of immobilized enzymes as well as good activity retentivity.

The DEAE-modified resin carrier of the present invention is a very good carrier in practical application especially because it can give an immobilized enzyme having good activity retentivity which is the most important factor in carrying out continuous operation for a long time by using immobilized enzymes. Other groups similar to DEAE groups such as dimethylaminoethyl groups of diisopropylaminoethyl groups can also be introduced into the resins to prepare similar resins. But, DEAE groups are found to be the best of all from standpoint of their easier modification reaction and affinity with enzymes.

Accordingly, it seems that the excellent characteristics of the DEAE-modified resin as enzyme-immobilization carrier are not owing to anion exchange capacity of DEAE groups but to specific affinity with enzyme molecules which is an inherent characteristic of DEAE group. This is further evidenced by the following fact. For example, a macroporous phenol-formaldehyde polycondensate resin having an anion exchange capacity of 7.10 meq/g-dry resin (ion-exchange capacity is estimated by batchwise neutralization titration after conditioning the resin to OH-form; the dry resin weight is obtained by weighing the resin after conditioning the resin to OH-form, followed by vacuum drying at the temperature of 60° C. for over 10 hours and standing at room temperature from 18° to 25° C. for more than 2 hours; the ion-exchange capacities mentioned hereinafter in the specification are all measured according to this method) modified with polyethylene polyamine (the number of recurring ethyleneamine units being not more than 4) has hydroxyl groups, primary amino groups and secondary amino groups on the resin and suitable for DEAE-modification. When this resin is subjected to DEAE-modification reaction under alkaline conditions, the increase in weight of the resin is sometimes greater than the increase in anion-exchange capacity by DEAE groups for some reason which has not yet been made very clear and it occurs that the total anion exchange capacity per unit weight of dry resin is decreased to less than 7.10 meq/g. For example, while there is increase of weight as much as 57.2% by DEAE-modification reaction, the total anion exchange capacity is 6.34 meq/g-dry resin with anion exchange capacity of DEAE groups being 1.82 meq/g-dry resin. Nevertheless when this DEAE-modified resin is used as carrier, the quantity of immobilized enzymes per unit weight is greater as compared with the case when the original carrier without DEAE-modification having 7.10 meq/g-dry resin is used as carrier. Further, the DEAE-modified resin can give immobilized enzymes having high activity with good activity retentivity, exhibiting superior characteristics of DEAE-modified resins as carrier. The effect of modification with DEAE groups is not therefore due to increase in anion exchange capacity but apparently to specific affinity with enzymes inherent in DEAE groups, the nature of which is not yet clarified in detail.

There is also an increase in volume of the resin together with increase in weight by DEAE-modification. Therefore, there is little change in volume per unit weight. For example, phenol-formaldehyde polycondensate resins with sizes of 16 mesh to 60 mesh screened through a sieve are packed in a column and a liquid is passed therethrough, the volume of the resin is between 3.0 ml and 4.0 ml per one gram of dry resin before and after modification with DEAE groups.

The DEAE-modified resin of the present invention can be prepared by reacting a compound of the formula:

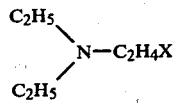

(wherein X is a halogen or hydrogensulfate) or its acid addition salt with a macroporous synthetic resin having functional groups reactive with said compound in the presence of an alkaline compound. It is important to carry out the reaction so that the resin may be wetted with the reaction mixture even at the internal portion of macropores in order to obtain DEAE-modified resins with a high degree of substitution.

DEAE-modification reagents represented by the formula

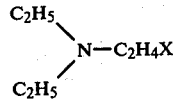

or its acid addition salt are preferably β-diethylaminoethyl chloride hydrochloride, β-diethylaminoethyl bromide hydrobromide and β-diethylaminoethyl hydrogensulfate, etc. From standpoint of reactivity and economy, β-diethylaminoethyl chloride hydrochloride is the most advantageous.

The amount of the DEAE-modification reagents to be used depends on the desired amount of DEAE groups introduced (degree of substitution), but a resin containing too small an amount of said groups is of little significance from the spirit of the present invention. It is generally advantageous to use an amount in excess of stoichiometry to carry out the reaction smoothly. But it is difficult to know precisely the number of moles of the resin and the number of functional groups reactive with the DEAE-modification reagents on the surface of the resin. Accordingly, in many cases, the empirically preferred amount of the DEAE-modification reagent is ⅛ part to 10 parts per one part of the dry resin, more preferably from ½ to 3 parts.

The alkaline compound to be used in the present invention includes alkali metal hydroxides such as sodium hydroxide or potassium hydroxide; alkaline earth metal hydroxides such as calcium hydroxide or magnesium hydroxide; and the like. In some cases, there may also be used organic amines such as triethylamine, etc. Preferable alkaline compounds are alkali metal hydroxides, among which sodium hydroxide is the most preferred.

The alkaline compound is added in an amount of 1/10 to 5 times as much as the moles of the DEAE-modification reagent. When it is necessary to remove the acid addition salt during the reaction, it is required to use the alkaline compound in an amount enough to neutralize the acid.

The synthetic resins to be used in the present invention may be any resin capable modification with DEAE groups having such groups as primary amino group, secondary amino group, hydroxyl group, imino group or sulfhydryl group. In compliance with the object of the present invention to provide a practically excellent enzyme-immobilization carrier for catalysts in industrial uses, the resin is desired to have in addition to the above functional groups a large number of macropores with pore sizes of about 100 Å to some 1000 Å as well as micropores which are formed depending on the extent of crosslinking, thus having a large pore volume and a large specific surface area. Such macropores are imparted physically by a specific polymerization method. The resins containing macropores are better in mechanical strength than those containing only micropores and suitable for continuous running. Macroporous resins are also referred to as MR type, MP type, macro-reticular structure or high-porous structure, etc. For the purpose of exhibiting a remarkable effect in immobilization of enzymes, the macroporous resins is desired to have a specific surface area of at least 1 m²/g-dry resin, very preferably 5 m²/g-dry resin or more (surface area of dry resin is measured by nitrogen adsorption method by means of a surface area measuring instrument, produced by Carlo-Erba Co., followed by data analysis by BET method to evaluate the values), a total volume of macropores with sizes from 100 Å to 2000 Å being at least 0.1 cc/g-dry resin, preferably 0.2 cc/g-dry resin (pore size and pore volume are measured by a mercury penetration type porosimeter produced by Carlo-Erba Co., data analysis being made to determine the values by supposing the shape of macropores as cylindrical with spherical cross-sectional area). Larger pores with sizes of 2000 Å or more will contribute little to dimensional stability of immobilized enzyme. The average pore size, which is different depending on the enzymes to be immobilized, is preferably from about 150 Å to about 1000 Å.

The macroporous resins satisfying the above requirements can be prepared by well-known methods but there are already many commercially available macroporous resins. Most of the commercially available resins, however, have hydroxyl groups, aliphatic primary amino groups or aliphatic secondary amino groups and there can scarcely been found those having sulfhydryl groups, imino groups or aromatic amino groups. Some examples of these macroporous resins are set forth in the following Table 1 together with physical and chemical properties thereof. The surface area and the pore volume of a resin do not undergo substantial changes after DEAE-modification reaction except for those within experimental errors.

so that the reactants may well be mixed but the resins may not be broken.

The anion exchange capacity based on DEAE groups (indicated by $C_D$) is represented by the following formula when the synthetic resin before introduction of DEAE groups is an anion exchange resin (of which ion-exchange capacity is indicated by $C_A$) and the total anion exchange capacity after introduction of DEAE groups is indicated by $C_T$:

$$C_D = C_T - C_A(X/Y)$$

wherein X represents the total weight of dry anion exchange resin before DEAE-modification reaction Table 1

| Trade name | Name of manufacturer | Matrix | Ion exchange groups | Functional groups utilized for DEAE-modification | Specific surface area ($m^2/g$) | Total* pore volume (cc/g) | Average pore diameter (Å) | Ion-exchange capacity (meg/g) |
|---|---|---|---|---|---|---|---|---|
| Duolite A-4 | Diamond Shamrock Chemical Co. | phenolic | tertiarized product of polyethylene polyamine | —OH | 68.1 | 0.563 | 250 | 4.38 |
| Duolite A-6 | " | " | " | —OH | 24.6 | 0.600 | 400 | 5.31 |
| Duolite A-7 | " | " | polyethylene polyamine | —OH, —$NH_2$ —NHR | 31.6 | 0.534 | 420 | 7.10 |
| Duolite S-30 | " | " | — | —OH | 90.3 | 0.605 | 340 | 0 |
| Duolite S-37 | " | " | partially tertiarized product of polyethylene polyamine | —OH, —NHR | 95.3 | 0.680 | 290 | 4.24 |
| Amberlite IR-45 | Rohm & Haas Co. | polystyrene | polyethylene polyamine | —$NH_2$, —NHR | 2.2 | 0.128 | 1,450 | 3.90 |
| Diaion WA-20 | Mitsubishi Chemical Industry Co. | polystyrene | polyethylene polyamine | —$NH_2$, —NHR | 4.6 | 0.290 | 330 | 4.20 |
| Diaion WA-21 | " | " | " | " | 5.1 | 0.325 | 560 | 4.75 |
| Sumichelate KA-800 | Sumitomo Chemical Co. | polyvinyl chloride | " | " | 15.0 | 0.375 | 1,400 | 4.12 |
| Diaion PA-418 (Comparison) | Mitsubishi Chemical Industry Co. | polystyrene | quaternary ammonium salt type II | —OH | 10.8 | 0.062 | 380 | 2.37 |
| Duolite A-162 (Comparison) | Diamond Shamrock Chemical Co. | " | " | " | <0.1 | <0.06 | — | 2.40 |

Note
All the properties are measured and calculated according to the method as described above.
*Total pore volume of macropores with sizes of 100 Å to 2,000 Å

While there is no particular upper limit of the specific surface area and the total pore volume, mechanical strength is insufficient when they are too great. Thus, the specific surface area is desired to be not more than 120 $m^2/g$ and the total pore volume not more than 80% of the total resin volume.

The reaction solvent is not particularly limited but an aqueous solvent, a non-aqueous solvent and a mixture of water with a non-aqueous solvent may employed. The reaction is carried out generally at not higher than 200° C. But the resins are liable to be broken and undesirable side reactions are liable to occur at too high temperature; the preferable reaction temperature is less than 100° C. The reaction rate is retarded at too low temperature. Thus, the most preferable temperature range is from around 10° C. to 80° C. Stirring may be conducted used and Y the total weight of dry resin after DEAE-modification reaction. The thus obtained $C_D$ is 0 to about 5 meq/g-dry resin and may sometimes show a negative value due to too great an increase in weight by DEAE-modification reaction. As mentioned above and apparently seen from the EXamples, excellent enzyme-immobilization carriers can be obtained even when the value of $C_D$ is approximately zero. Thus, it cannot simply be determined from $C_D$ value only whether DEAE-modified resin carrier is good or not. Another criterion for judgement of goodness of DEAE-modified resin carrier the production Z of increase in weight by DEAE-modification reaction:

$$Z = (Y/X - 1) \times 100(\%)$$

In consequence, when the resin to be subjected to DEAE-modification has already anion exchange capacity, it is preferred to satisfy at least one of the requirements $C_D \geqq 0.5$ meq/g and $Z \geqq 10$, more preferably $C_D \geqq 1.0$ meq/g and $Z \geqq 20$. Most preferably, at least one of the requirements $C_D \geqq 1.5$ meq/g and $Z \geqq 30$ should be satisfied.

On the other hand, when DEAE groups are introduced into a synthetic resin having only hydroxyl groups or sulfhydryl groups as functional groups reactive with DEAE-modification reagents and no anion exchange capacity in itself (irrespective of whether it has cation exchange capacity), it naturally follows that $C_D$ is equal to $C_T$, and $C_D$ is desired to be not less than 1.0 meq/g, more preferably not less than 2.0 meq/g to give excellent enzyme-immobilization carrier. When a large quantity of DEAE groups cannot be introduced by one reaction, the modification reaction is preferably repeated twice or three times. But when the resin to be subjected to DEAE-modification is an anion exchange resin of strongly basic type II containing no functional group other than hydroxyl groups in quaternary ammonium salts, it is difficult to introduce a large quantity of DEAE groups thereinto. A resin having DEAE groups as well as other anion exchange groups is generally better as enzyme-immobilization carrier than a resin having only DEAE groups as anion exchange groups.

One of the particular features of the DEAE-modified macroporous resin in the present invention as enzyme-immobilization carrier is that immobilization by covalent attachment method as well as by adsorption method is possible, so long as some of hydroxyl groups, primary amino groups or secondary amino groups remain unaltered in the resin.

Preparation of the immobilized enzymes by adsorption method can be carried out according to conventional methods. For example, DEAE-modified resin is treated with an aqueous acid or an alkali solution with concentration of 0.02 M to 3 M to activate DEAE groups or alternatively it is buffered at near the pH range for enzyme action with a buffer solution (with concentration of about 0.02 M to 3 M), followed by thorough washing, and then the DEAE-modified resin is immersed in a solution of enzymes to be immobilized for sufficient time (it is thereby important that the resin should be wetted to the internal portion of macropores with the solution), followed by stirring if desired and further by filtration and washing to immobilization. The temperature for adsorption immobilization should be not higher than 40° C. unless the enzyme is heat-resistant. It is more preferably about 10° C. or lower. The thus prepared immobilized enzyme can generally contain about 100 mg or more of enzyme proteins per one gram of dry carrier and is stable if it is not washed with a saltous solution having strong ionic strength. The enzymes to be immobilized on the carrier according to the present invention may include not only those consisting only of simple proteins but also enzymes which require co-enzymes. Further, not only one kind of enzymes but also two or more different kind of enzymes can simultaneously be immobilized.

On the other hand, in case of covalent attachment method, there can be applied various attachment methods in which reactivity of hydroxyl groups, primary amino groups or secondary amino groups present in DEAE-modified resin carrier is utilized. In particular, there may be mentioned such methods as relatively simple methods among covalent attachment methods to give stable immobilized enzymes as (1) an attachment method by s-triazynyl derivative using cyanuric chloride or its derivative, (2) an attachment method using glutaraldehyde and (3) an attachment method using a carbodiimide reagent. In case of immobilization by covalent attachment method, the amount of enzymes to be immobilized per unit weight of the carrier is smaller than in case of immobilization by adsorption method, but there can be obtained a carrier excellent in specific activity of immobilized enzymes and activity retentivity.

Typical examples of enzymes which can be immobilized on the present carrier are alcohol dehydrogenase, aspartate aminotransferase, asparaginase, aspartate decarboxylase, amino acid racemase, asparagine synthetase, D-amino acid oxidase, amino acylase, $\alpha$- and $\beta$-amylase, adenosine deaminase, amylo-glucosidase, aspartase, bromelain, catalase, cellulase, cholinesterase, chymotrypsin, colagenase, deoxyribonuclease, dextranase, ficin, fumarase, galactose oxidase, $\beta$-galactosidase, glucose isomerase, glucose oxidase, glutaminase, glutamate dehydrogenase, hesperidinase, hexokinase, invertase, inulase, lactase, esterase, lactate racemase, lipase, lysozyme, papain, pronase, pepsin, penicillin amidase, pectinase, phosphatase, phosphorilase, maltase, protease, ribonuclease, melibiase, phenol oxidase, tannase, tyrosinase, trypsin, urease, uricase, and so on.

When adsorption method is used, enzymes with isoelectric points more acidic than the optimum pH range are preferred. For example, there may be mentioned pronase, amino acylase, glucose isomerase, $\beta$-galactosidase (lactase), ribonuclease, $\beta$-amylase, iso-amylase, pullulanase, urease, deaminase, lipase, esterase, etc. In covalent attachment method, any enzyme can be used except for those which lose enzymatic activity by immobilization.

The present invention is illustrated in further detail with reference to the following Examples, by which the present invention is not limited but various modification can be made without departure from the spirit of the invention.

EXAMPLE 1

In a pressure beaker, 13.8 g of sodium hydroxide is dissolved in 60 ml of water (the word "water" hereinafter all refer to distilled water). In this solution is immersed 20.0 g of dry Duolite A-7 and degassing is conducted by aspirator for about 50 minutes while cooling the mixture with ice-water. Then, while rinsing the resin and the sodium hydroxide solution with 200 ml of water, they are transferred into a flask of 500 ml capacity. Stirring slowly the mixture, 180 ml of aqueous solution having 50.0 g of $\beta$-diethylaminoethyl chloride hydrochloride (DEAEC.HCl) dissolved therein is added dropwisely by a dropping funnel over 2 hours. The reaction temperature is raised gradually from initiation of the dropwise addition from 20° C. to about 50° C. after one hour and thereafter maintained at said temperature. After completion of the dropwise addition, stirring is further continued for three hours before the reaction mixture is filtered and the resin is washed with water, 0.5 M aqueous nitric acid solution, water, 0.5 M aqueous sodium hydroxide solution, water, 0.5 M aqueous nitric acid solution, water and 0.5 M aqueous sodium hydroxide solution, successively in the order just mentioned. The resin is further washed thoroughly with water until pH of waste washing is 6.9. The resin is then dried by the method as described above and the total resin is weighed to be 28.9 g, namely Z=44.5%. From the measured total anion exchange capacity of 6.74 meq/g, the anion exchange capacity based on DEAE groups is calculated as 1.80 meq/g.

EXAMPLE 2

The same Duolite A-7 and amount of DEAEC.HCl as in Example 1 are used. In the following, there are set forth only the amounts and conditions different from Example 1. Namely, 14.0 g of sodium hydroxide is dissolved. While rinsing the resin together with the sodium hydroxide solution with about 50 ml of water, they are transferred into a flask of 500 ml capacity. In a reaction mixture already maintained at 62° C., a solution of 50 g of DEAEC.HCl dissolved in 70 ml of water is added dropwisely over 2 hours. The temperature of the reaction mixture is raised up to 68° C. one hour after initiation of the dropwise addition. After completion of the dropwise addition, the reaction mixture is maintained at from 55° to 60° C. to carry out the reaction for total of 7 hours. Then, similarly as in Example 1, the resin is filtered, washed and dried. The total amount of the resin is measured to be 39.5 g, Z=97.5%. The total anion exchange capacity is found to be 3.50 meq/g and $C_D$ calculated to be −0.09 meq/g. Considering experimental errors, $C_D$ is approximately 0 meq/g. Measurement of water content at the time of drying shows that the starting Duolite A-7 contains 0.084 g water/g-dry resin and said DEAE-modified Duolite A-7 0.0837 g water/g-dry resin, indicating substantially the same value within experimental errors. Hence, the great increase in weight in this Example seems to be due to unknown side reactions as well as normal DEAE-modification reaction.

EXAMPLE 3

While cooling a solution of 7.2 g of sodium hydroxide dissolved in about 35 ml of water with ice-water, 10.0 g of Duolite A-7 is immersed therein and degassing is conducted by aspirator for one hour. Then the resin and the sodium hydroxide solution are transferred into a flask of 300 ml capacity, while rinsing with about 35 ml of water, and 60 ml of an aqueous solution having 18.1 g of DEAEC.HCl dissolved therein is added dropwisely over one half hour into the resin-sodium hydroxide solution maintained at 55° to 60° C. under continuous stirring. Seven hours after initiation of the dropwise addition, the reaction is discontinued, followed by filtration, washing and drying similarly as in Example 1 to find the total weight=15.72 g and Z=57.2%. $C_T$ is found to be 6.34 meq/g, from which $C_D$ is calculated to be 1.82 meq/g.

EXAMPLE 4

In 25 ml of 4 N aqueous sodium hydroxide solution is immersed 4.0 g of thoroughly washed and dried Duolite S-30. After degassing for about 30 minutes by aspirator under cooling at 2° C. to 4° C., the mixture is transferred into a flask by rinsing with about 20 ml of water. While stirring is continued slowly, and maintaining the reaction temperature at 50° C. to 60° C., 28 ml of an aqueous solution having dissolved 7.6 g of β-diethylaminoethyl bromide hydrobromide (DEAEB.HBr) is added dropwisely to the mixture over one hour. The reaction is discontinued after 6 hours after initiation of the dropwise addition, followed by filtration, washing and drying as in Example 1. The proportion of increase in weight is found to be 10.5%, with $C_T=C_D=1.57$ meq/g.

Using the thus DEAE-modified Duolite S-30 as starting material (4.42 g), the second reaction is repeated similarly as in the above first reaction, whereby the total amount of resin obtained is found to be 4.73 g with $C_D$ 2.48 meq/g. Further, the third DEAE-modification reaction is repeated using the DEAE-modified Duolite S-30 obtained in the second reaction as starting material, whereby the total amount of the resin is found to be 5.04 g, with $C_D$ 2.74 meq/g.

EXAMPLES 5-20

In the following Table 2 are shown in conditions for preparation of various carriers and the results obtained. The amount of water used shows total amount of water used in the reaction. Under otherwise specifically noted, the starting resin is immersed in an aqueous alkaline compound solution, followed by degassing under cooling with ice-water for 30 minutes to one hour. The reaction time shows that from initiation of the dropwise addition to filtration of the resin. Filtration, washing and drying are conducted in the same manner as in Example 1.

Table 2

| Example No. | Starting resin | Weight of resin (g) | Weight of NaOH (g) | Weight of DEAEC.HCl (g) | Amount of water (ml) | Initial reaction temp. (°C.) | Reaction temp. (°C.) | Time to reach reaction temp. (hr) | Time for DEAEC.HCl addition (hr) | Reaction time (hr) | Y (g) | Z (%) | $C_T$ (meq/g) | $C_D$ (meq/g) |
|---|---|---|---|---|---|---|---|---|---|---|---|---|---|---|
| 5 | Duolite S-37 | 10.0 | 6.9 | 25.0 | 340 | 22 | 55–60 | 1.0 | 1.75 | 6 | 12.63 | 26.3 | 4.45 | 1.10 |
| 6 | Duolite A-6 | 20.0 | 13.8 | 50.0 | 420 | 20 | 60 | 1.0 | 2.0 | 6 | 22.0 | 10.0 | 4.82 | 0 |
| 7 | Duolite A-6 | 10.0 | 10.0(1) | 33.6(2) | 280 | 20 | 60 | 1.5 | 1.75 | 6 | 12.4 | 24.0 | 5.74 | 1.45 |
| 8 | Duolite A-4 | 9.9 | 6.3 | 25.8 | 200 | 20 | 20 ± 2 | — | 2.0 | 12 | 12.36 | 25 | 4.83 | 1.25 |
| 9 | Duolite A-7 | 7.0 | 6.0 | 25.8 | 180 | 20 | ~20 | — | 0 | 10 | 9.26 | 40 | 7.09 | 2.0 |
| 10 | Duolite S-37 | 7.0 | 6.3 | 29.6(3) | 180 | 20 | ~20 | — | 1.75 | 10 | 8.20 | 17.1 | 4.70 | 1.08 |
| 11 | Duolite A-7 | 5.0 | 3.5 | 12.0 | 75 | 22 | ~22 | — | 1.0 | 10 | 6.6 | 32.0 | 8.10 | 2.73 |
| 12 | Duolite A-4 | 6.0 | 7.2 | 15.5 | 80 | 22 | 90–95 | 0.5 | 0.75 | 2 | 7.1 | 18.5 | 4.90 | 1.12 |
| 13 | Diaion A-21 | 10.0 | 6.9 | 18.1 | 76 | 23 | ~60 | 1.5 | 1.5 | 7 | 10.6 | 6.0 | 6.19 | 1.69 |

Table 2-continued

| Example No. | Starting resin | Weight of resin (g) | Weight of NaOH (g) | Weight of DEAEC. HCl (g) | Amount of water (ml) | Initial reaction temp. (°C.) | Reaction temp. (°C.) | Time to reach reaction temp. (hr) | Time for DEAEC. HCl addition (hr) | Reaction time (hr) | Y (g) | Z (%) | $C_T$ (meq /g) | $C_D$ (meq /g) |
|---|---|---|---|---|---|---|---|---|---|---|---|---|---|---|
| 14 | Amberlite IR-45 | 10.0 | 7.5 | 18.1 | 100 | 22 | ~60 | 1.0 | 0 | 6 | 10.95 | 9.5 | 5.03 | 1.47 |
| 15 | Diaion WA-20 | 10.0 | 11.5(4) | 35.0(5) | 120 | 20 | 60 | 0.5 | 1.75 | 6 | 10.84 | 8.4 | 5.65 | 1.82 |
| 16 | Sumichelate KA-800 | 10.0 | 7.5 | 30.0(6) | 120 | 20 | 60 | 0.5 | 1.75 | 6 | 11.5 | 15.0 | 5.88 | 2.30 |
| 17 | Sumichelate KA-800 | 10.0 | 9.0 | 25.0 | 150 | 60 | 60 | — | 1.50 | 6 | 11.8 | 18.0 | 5.39 | 1.90 |
| 18 | Duolite A-7 | 10.0 | 6.3 | 18.0 | acetone 70 + 70 | 20 | 20 | — | 2.0 | 12 | 13.9 | 39.0 | 8.11 | 3.00 |
| 19 | Diaion WA-21 | 10.0 | 6.9 | 18.1 | methanol 70 + 70 | 20 | 20 | — | 2.0 | 10 | 11.8 | 18.0 | 6.90 | 2.87 |
| 20 | Duolite A-7 | 5.0 | 3.5 | 12.0 | dioxane 50 + 50 | 20 | 20 | — | 1.5 | 10 | 7.1 | 42.0 | 8.05 | 3.05 |
| Comparison example 1 | Duolite A-162 | 10.0 | 7.5 | 18.1 | 100 | 20 | 60 | 1.0 | 1.5 | 6 | 10.1 | 1.0 | 2.40 | 0.02 |
| Comparison example | Diaion PA-418 | 10.0 | 7.5 | 18.1 | 100 | 20 | 60 | 0.75 | 2.0 | 6 | 10.15 | 1.5 | 2.42 | 0.09 |

Remarks
(1) KOH
(2) DEAEB . HBr
(3) DEAEHS*
(4) KOH
(5) DEAEHS
(6) DEAEB . HBr
*β-diethylaminoethyl hydrogensulfate In the following, immobilization of enzymes on the carriers of the present invention and some reaction experiments are shown. In the Experiments set forth below, specific activity of glucose isomerase, protein content and fructose content are determined by the following methods:

(1) Measurement of activity

To a glucose isomerase solution are added 0.1 M D-glucose, 0.05 M phosphate buffer solution and 0.005 M MgSO$_4$.7H$_2$O and, while maintaining pH at 7.0, the reaction is carried out at 70° C. for one hour. The amount of fructose formed is measured. One unit of activity is expressed as the amount of enzymes necessary for forming 1 mg of fructose under the above conditions.

The activity of immobilized glucose isomerase is determined by measuring the fructose contained in filtrate when the reaction is carried out with slow stirring under the same reaction conditions as described above except that immobilized glucose isomerase is added in place of glucose isomerase solution, followed by filtration of the reaction mixture. The amount of immobilized glucose isomerase necessary for forming 1 mg of fructose is determined as one unit.

(2) Measurement of fructose content

Fructose content is determined quantitatively from absorption strength at 560 nm after 30 minutes by cysteine carbazol sulfate method at 30° C. Under said conditions, the percentage of color formation by glucose is about 1/200 of that by fructose and negligible.

(3) Measurement of protein content

With reference to "Seikagaku Jikken Koza" (Biochemical Experiment Course) Vol. 5, page 27, quantitative analysis is carried out by Lowry method. The calibration curve is made by using crystalline bovine serum albumin (250 μg/ml-solution).

Experiment 1

There is prepared 30 ml of a 0.05 M phosphate buffer solution (pH 7.65, containing 0.005 M MgSO$_4$.7H$_2$O) containing 45,330 units of glucose isomerase, (protein content: 399 mg), which is purified by acetone fractionation from a ultrasonic crushed suspension of living microorganism cells belonging to genus Streptomyces (produced by Nagase Sangyo Co.). In this solution is immersed 3.0 g. of the DEAE-modified Duorite A-7 prepared in Example 1 and immobilization is carried out at 20° C. for 16 hours under shaking at 80 r.p.m.

After immobilization, immobilized glucose isomerase is separated by filtration and washed with 0.2 M phosphate buffer solution (pH 7.65) and water. From the activity of the resultant filtrate, the amount of immobilized enzyme is calculated to find that 41,750 units of glucose isomerase are immobilized. The percentage of immobilization of activity is 92.1%.

Similarly, from the protein content in the filtrate, the amount of protein immobilized is found to be 333.4 mg, with immobilization percentage of 83.3%. This immobilized enzyme is packed in a column (diameter: 15 mm) equipped with a jacket and 3 M purified glucose solution is flown at $SV=2.5$ $hr^{-1}$ while maintaining the column temperature at 60° C. Conversion to fructose 20 hours after commencement of flowing is found to be 50.4%.

Reference experiment 1

Experiment 1 is repeated except that unmodified Duolite A-7 is used in place of the DEAE-modified Duolite A-7 prepared in Example 1, whereby the immobilized activity is found to be 19,800 units, with immobilized protein content being only 167 mg. When this immobilized enzyme is packed in a column and a 3 M purified glucose solution is passed through said column at 65° C. at $SV=5.5$ $hr^{-1}$, the conversion is found to be 19.0%.

Experiments 2–11

Purified glucose isomerase extracted from living microorganism cells belonging to genus Streptomyces is immobilized on various carriers under the same conditions as in Experiment 1 to give the results as shown in Table 3. In Table 3, the carrier numbers correspond to those of Examples.

sodium chloride solution, 0.1 M phosphate buffer solution and ice-cooled water in this order until there is detected no protein in wash. From activities and protein content in wash, the immobilized activity is found to be 17,500 units (86%) with immobilized protein content of 121 mg (81%).

Experiment 13

In a solution having 200 mg of commercially available enzyme pronase E originated from *Streptomyces griseus* dissolved in 25 ml of a 0.05 M phosphate buffer solution of pH 7.0 maintained at 4° C., there is immersed 2.0 g of the DEAE-modified Duolite A-7 prepared in Example 1. The mixture is slowly stirred at about 4° C. for 8 hours under suction by aspirator to immobilize the enzyme by adsorption. The immobilized pronase E is thoroughly washed with 0.05 M phosphate buffer solution of pH 6.0 and then with water. The immobilized enzyme protein is found to be 182 mg. Specific activity of the immobilized enzyme is measured at 40° C. and pH 6.0 by pH-stat (Hiranuma Seisakusho, Model pS-11) using 20% DL-lysine methyl ester as substrate to be 3.42 μmoles/mg.min, which corresponds to 57% of the specific activity of the solution enzyme.

Experiment 14

Pronase E is immobilized by covalent attachment method under the same conditions and procedure as in Table 3

| | | | Enzyme activity charged (unit) | Immobilized enzyme activity (unit)* | Reaction of 3M purified glucose solution through column | | | |
|---|---|---|---|---|---|---|---|---|
| Experiment No. | Carrier No. | Carrier weight (g) | | | pH | SV (hr-1) | Temperature (°C.) | Conversion to fructose after 20–24 hours |
| 2 | 2 | 3.0 | 45,330 | 41,980 | 7.65 | 3.5 | 65 | 50 |
| 3 | 3 | 3.0 | 44,100 | 40,770 | 7.65 | 3.5 | 60 | 50 |
| 4 | 9 | 3.0 | 21,530 | 20,540 | 8.2 | 2.5 | 60 | 50.5 |
| 5 | 6 | 1.0 | 8,610 | 6,690 | 7.65 | 2.0 | 65 | 52 |
| 6 | 5 | 1.0 | 8,610 | 7,700 | 8.2 | 2.5 | 60 | 50.5 |
| 7 | 8 | 1.0 | 7,400 | 6,100 | 7.65 | 2.0 | 60 | 50 |
| 8 | 4 | 2.0 | 22,700 | 20,800 | 8.2 | 3.0 | 60 | 50 |
| 9 | 13 | 2.0 | 22,700 | 19,100 | 8.2 | 2.5 | 60 | 49.5 |
| 10 | 14 | 2.0 | 22,700 | 18,900 | 8.2 | 2.5 | 60 | 50 |
| 11 | 16 | 1.0 | 7,400 | 7,100 | 7.65 | 2.0 | 60 | 50 |

*calculated from units in wash

Experiment 12

In 20 ml of 1 N aqueous sodium hydroxide solution is immersed 2.0 g of the DEAE-modified Duolite A-7 prepared in Example 1 and, after degassing at 4° C. for 15 minutes, excessive alkaline solution is removed by filtration. This resin is immersed in 25 ml of dioxane at room temperature for 5 minutes and, after stirring the mixture, 20 ml of dioxane solution containing 4 g of cyanuric chloride prepared beforehand is added thereto, followed by vigorous stirring at room temperature. After three minutes, 25 ml of cold water is added to the reaction mixture and, after 5 seconds, 25 ml of acetic acid is further added thereto to terminate the reaction. The mixture is quickly washed with cold water and cold acetone. The resultant resin is added to a phosphate buffer solution of pH 7.8 containing 20,400 units (protein content 149 mg) of glucose isomerase. Immobilization reaction is conducted with stirring for 5 hours while maintaining the temperature at 2° C. to 4° C. and maintaining pH at 7.8 by addition of 0.2 N sodium hydroxide solution. Immobilized enzyme is separated by filtration and washed with ice-cooled 5 M Experiment 12 except that 2.0 g of the DEAE-modified Duolite A-4 prepared in Example 12 is used in place of 2.0 g of the DEAE-modified Duolite A-7 in Experiment 12 and 120 mg of pronase E in place of 20,400 units of glucose isomerase. The amount of immobilized enzyme is found to be 95.8 mg/g-carrier and specific activity 2.90 μmoles/mg.min, as measured by pH-stat at pH 6.0 and 40° C. using 20% DL-lysine methyl ester as substrate.

Experiments 15–19

Several examples of pronase E immobilized on the carriers of the present invention are shown below in Table 4. The adsorption method in the column of immobilization method in said Table refers to a similar procedure same as described in Experiment 13 and covalent attachment method to a similar procedure as in Experiment 14 using cyanuric chloride. The numbers of carriers correspond to those of Examples. All of the specific activities are measured by pH-stat under the conditions of pH 6.0 at 40° C., using 20% DL-lysine methyl ester solution as substrate.

Table 4

| Experiment No. | Carrier No. | Immobilization method | Amount of carrier (g) | Amount of enzymes charged (mg) | Amount of enzymes immobilized (mg/g-carrier) | Specific activity (μmoles/min . mg) |
|---|---|---|---|---|---|---|
| 15 | 13 | Adsorption method | 2.0 | 200 | 65 | 2.72 |
| 16 | 14 | " | 2.0 | 200 | 61 | 2.75 |
| 17 | 7 | Covalent attachment method | 1.0 | 120 | 105 | 1.91 |
| 18 | 1 | " | 1.0 | 115 | 73 | 4.86 |
| 19 | 5 | " | 1.0 | 100 | 78 | 3.48 |

EXPERIMENT 20

Immobilization of lactase is effected according to the same covalent attachment method with cyanuric chloride as in Experiment 12 using 100 mg of lactase produced by *Asperigillus oryzae* and 1.0 g of the DEAE-modified Duolite A-7 prepared in Example 2. After thorough washing of the immobilized enzyme, the amount of immobilized enzyme is measured to be 66.7 mg protein/g-carrier and specific activity is measured at pH 4.5 and 30° C. using 5% lactose as substrate to be 5.2μ moles/mg.min, which corresponds to 30% of the activity of the solution enzyme (solution activity: 17.3μ moles/mg.min).

EXPERIMENT 21

Lactase produced by *Aspergillus oryzae* (different in degree of purification from that of Experiment 20, with solution activity of 10.2μ moles/mg.min at pH 4.5 and 30° C.), 165 mg, is dissolved in 10 ml of a phosphate-citrate buffer solution of pH 4.5 with concentration of about 0.02 M which is maintained at 4° C. In this solution is immersed 1.0 g of the DEAE-modified Duolite S-37 prepared in Example 5 and immobilization is effected under shaking at 80 r.p.m. for 16 hours while maintaining the temperature at about 4° C. After immobilization, the immobilized enzyme is washed with phosphate-citrate buffer solution with a concentration of about 0.05 M and the same pH, and then with water. The amount of the immobilized enzyme is found to be 123 mg and specific activity, at pH 4.5 and 30° C. using 5% lactose as substrate, is measured to be 2.1μ moles/mg.min.

EXPERIMENT 22

Lactase produced by *Aspergillus oryzae* (enzyme activity in solution of 17.3μ moles/mg.min, at pH 4.5 and 30° C.), 200 mg, is dissolved in 10 ml of a phosphatecitrate buffer solution maintained at 4° C. with a concentration of about 0.02 M and pH 5.5. In this solution, there is immersed 1.0 g of the DEAE-modified Duolite A-7 prepared in Example 3 and immobilization is effected under shaking at 80 r.p.m. for 18 hours while maintaining the temperature at about 4° C. The amount of the immobilized enzyme, after washing thoroughly with a phosphate-citrate buffer solution with a concentration of about 0.05 M and pH 5.5 and then with water, is found to be 149 mg. Specific activity is measured to be 2.1μ moles/mg.min. at pH 5.5 and 30° C. using 5% lactose as substrate.

EXPERIMENT 23

A commercially available β-amylase produced from soybean (produced by Nagase Sangyo Co.; $1.5 \times 10^4$ unit*/g), 300 mg, is dissolved in 300 ml of a 0.02 M acetate buffer solution of pH 5.0 and insolubles are separated by centrifugation. In the resultant supernatant is thrown 2.0 g of the DEAE-modified Diaion WA-21 prepared in Example 13. After degassing by aspirator, immobilization is effected under shaking at 80 r.p.m. for 16 hours while maintaining the temperature at about 4° C. After thorough washing with the above acetate buffer solution and water, the amount of the immobilized enzyme is found to be 121 mg/g-carrier. This immobilized enzyme is packed in a column equipped with a jacket and, while maintaining the column at 50° C., a substrate of 2% soluble starch solution is flown at $SV = 0.4$ hour$^{-1}$. The increase in amount of reducing sugar is measured by Somogyi-Nelson method to determine the amount of maltose formed. The amount of maltose in effluent is found to be 11.5 mg/ml-solution. Under these conditions, continuous reaction is performed for 10 days. The amount of maltose in the effluent on the 10th day is found to be 11.3 mg/ml, showing that there is little change.

*) 1 unit represents activity which can form a reducing power corresponding to 100 γ of glucose at pH 4.5, 40° C. for one minute.

EXPERIMENT 24

Experiment 23 is repeated except that the DEAE-modified Duolite A-7 prepared in Example 1 is used in place of the carrier prepared in Example 13. The amount of immobilized enzyme is found to be 129 mg/g-carrier. When continuous reaction is performed in the same manner as in Experiment 23, the amount of maltose in the first day is found to be 11.9 mg/ml-solution, while that on the 10th day to be 12.0 mg/ml.

EXPERIMENT 25

Pllulanase produced by *Aerobacter aerogenes* (produced by Nagase Sangyo Co.), 200 mg, is immobilized on the DEAE-modified Amberlite IR-45 prepared in Example 14 by the same method as in Experiment 23. The amount of enzyme immobilized is found to be 58.5 mg/g-carrier. This immobilized enzyme, 2 g, is immersed in 25 ml of a 0.5% pullulane solution. After shaking at 80 r.p.m. at pH 5.0 and 40° C. for 30 minutes, the amount of maltotriose in the filtrate is measured by Somogyi-Nelson method to find that the conversion to maltotriose is about 97%.

EXPERIMENT 26

The DEAE-modified Duolite A-4 prepared in Example 8, 2.0 g is equilibrated with 0.05 M Veronal buffer solution of pH 7.0 and then immersed in 30 ml of 0.05 M Veronal buffer solution containing 300 mg of aminoacylase produced by *Aspergillus oryzae* to effect immobilization at about 4° C. under shaking at 80 r.p.m. for 15 hours. The amount of the immobilized enzyme is calculated from the filtrate as 97 mg/g-carrier. This aminoacylase is packed in a column of 10 mm in diameter equipped with a jacket and, while maintaining the column temperature at 40° C., 0.2 M N-acetyl-DL-methionine solution (pH 7.0, containing $1\times10^{-4}$ M $CoCl_2$) is flown through the column continuously. The percentage of hydrolysis of L-isomer after 24 hours is 100% and there is observed no loss in activity even after 10 days.

EXPERIMENT 27

A commercially available adenylic deaminase (produced by Amano Seiyaku Co., 50,000/g) for producing inosinic acid, 400 mg, is dissolved in 50 ml of a phosphate buffer solution of about 0.02 M concentration (pH 5.6) maintained at about 4° C. In this solution is immersed 4.0 g of the DEAE-modified Duolite A-7 prepared in Example 3. After degassing by aspirator, immobilization is effected under shaking at 80 r.p.m. at about 4° C. for 16 hours. The amount of the enzyme immobilized is found to be 72 mg/g-carrier. This immobilized enzyme is packed in a column (diameter: 15 mm) equipped with a jacket and, while maintaining the temperature at 50° C., 1% adenylic acid solution is flown through the column at $SV=1.1$ hour$^{-1}$ for 4 days, whereby there is observed no loss in activity even after 100 hours.

APPLICATION EXAMPLES

In the following, there are shown various application examples. Application examples 1 to 5 are the experiments of continuous isomerization reaction using a column of glucose isomerase immobilized on the carrier of the present invention. Application examples 6 to 8 are experiments in which batch reactions using immobilized pronase E are repeated. Application examples 9 and 10 are experiments in which batch reactions using immobilized lactase are repeated. The results are shown in Tables 5 to 7. The numbers of Experiments show that the immobilized enzymes prepared and measured for their activities in the Experiments as set forth above are used.

In case of glucose isomerase, it is packed in a column and 3 M (54 W/V %) purified glucose is passed therethrough under the same conditions as described in the above Experiments. Accordingly, SV is maintained constant until the end of the column operation and the time at which conversion of fructose becomes half of that at the initial stage (shown in Table 3 as that after 20–24 hours) is determined as the half-life time. The amount of purified glucose solid components treated per 1 g of the immobilized enzyme by the time at which conversion to fructose becomes ¼ of that at the initial stage is determined as the productivity. When the carrier according to the present invention is employed, activity retentivity is very good and productivity is very high as seen in Table 5.

In case of immobilized pronase, 10 ml of 10% L-lysine methyl ester is used as substrate and each about 100 mg of the immobilized enzyme prepared in corresponding Experiments is used. The experiments are repeated by batch methods. The experiment time is 40 minutes per one experiment and the number of experiments by which the reaction rate measured by pH-meter becomes half of that of the first experiment is determined as the half-life number.

In case of immobilized lactase, about 100 mg of immobilized enzyme is used and, using 10 ml of 5% lactase solution as substrate, the reaction is carried out by batch method under shaking at 80 r.p.m. for 30 minutes for each experiment. The activity is measured from the amount of glucose formed. This experiment is repeated under otherwise the same conditions as described in the above Experiments.

Table 5

Continuous isomerization reaction through column

| Application example No. | Experiment No. | Half-life time for activity (days) | Productivity (g sugar solid/g immobilized enzyme) |
|---|---|---|---|
| 1 | 1 | 95 | 20,500 |
| 2 | 2 | 43 | 13,150 |
| 3 | 3 | 53 | 16,600 |
| 4 | 5 | 48 | 12,800 |
| 5 | 8 | 46 | 14,800 |

Table 6

Repeated reactions using immobilized pronase

| Application example No. | Experiment No. | The number of experiments at which the activity is reduced to half-value (half-life number) |
|---|---|---|
| 6 | 14 | 90 |
| 7 | 18 | 50 |
| 8 | 19 | 25 |

Table 7

Repeated reactions using immobilized lactase

| Application example No. | Experiment No. | The number of experiment at which the activity is reduced to half-value (half-life number) |
|---|---|---|
| 9 | 20 | 69 |
| 10 | 22 | 38 |

What is claimed is:

1. An enzyme-immobilization carrier which comprises a macroporous, synthetic anion-exchange resin having a specific surface area of at least 1 m$^2$/g-dry resin and containing macropores with a pore size of 100 Å to 2,000 Å, of which total volume is at least 0.1 cc/g-dry resin; said resin comprising (a) a phenol-formaldehyde condensate matrix and diethylaminoethyl groups linked to the matrix through an ether linkage, wherein the ion-exchange capacity of the resin is not less than 1 meq/g-dry resin, (b) a phenol-formaldehyde condensate matrix having primary amino groups, secondary amino groups or a mixture thereof as an anion-exchanger and diethylaminoethyl groups linked to the matric through an ether linkage or to said primary or secondary amino groups to form a secondary or tertiary amino group respectively, wherein the ion-exchange capacity due to the diethylaminoethyl groups is not less than 0.5 meq/g-dry resin and the total ion-exchange capacity is not less than 1 meq/g-dry resin, or (c) a crosslinked polystyrene matrix having primary amino groups, secondary amino groups or a mixture thereof as an anion-exchanger and diethylaminoethyl groups linked to said primary or secondary amino group to form a secondary or tertiary amino group respectively, wherein the ion-exchange capacity due to the diethylaminoethyl groups is not less than 0.5 meq/g-dry resin and the total ion-exchange capacity is not less than 1 meq/g-dry resin.

2. An enzyme-immobilization carrier as in claim 1, wherein the specific surface area of the resin is 5 m²/g or more.

3. An enzyme-immobilization carrier as in claim 1, wherein the average pore size of the pores in the synthetic resin is from about 150 Å to about 1,000 Å.

4. An enzyme-immobilization carrier as in claim 1, wherein the volume of macropores with pore sizes from 100 Å to 2,000 Å is 0.2 cc/g or more.

5. An enzyme-immobilization carrier as in claim 1, wherein the resin further contains other anion exchange groups.

6. A process for producing an enzyme-immobilization carrier comprising a synthetic anion exchange resin having diethylaminoethyl groups, which comprises reacting a diethylaminoethyl derivative of the formula:

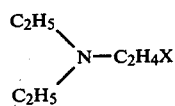

wherein X is halogen or hydrogensulfate or its salts with granules of a solid phenol-formaldehyde resin of a macroporous type having no other functional groups besides OH groups, primary amino groups, and/or secondary amino groups and tertiary amino groups in addition to OH group (not including said diethylaminoethyl groups), or with beads of a crosslinked polystyrene resin of a macroporous type having primary amino groups and/or secondary amino groups and tertiary amino groups, having a specific surface area of at least 1 m²/g-dry resin and containing macropores of which the total volume of those with pore sizes from 100 Å to 2,000 Å is at least 0.1 cc/g-dry resin in the presence of an alkaline compound.

7. A process as in claim 6, wherein the diethylaminoethyl derivative or its salt is β-diethylaminoethyl chloride hydrochloride, β-diethylaminoethyl bromide hydrobromide or β-diethylaminoethyl hydrogensulfate.

8. A process as in claim 7, wherein the diethylaminoethyl derivative salt is β-diethylaminoethyl chloride hydrochloride.

9. A process as in claim 6, wherein the amount of the diethylaminoethyl derivative or its salt is used in an amount of ½ to 10 parts per one part of the dry resin.

10. A process as in claim 9, wherein the diethylaminoethyl derivative or its salt is used in an amount of ½ to 3 parts per one part of the dry resin.

11. A process as in claim 6, wherein the alkaline compound is an alkali metal hydroxide, an alkaline earth metal hydroxide or an organic amine.

12. A process as in claim 11, wherein the alkaline compound is sodium hydroxide.

13. A process as in claim 6, wherein the amount of the alkaline compound added is from 1/10 to 5 times moles as much as that of the diethylaminoethyl derivative or its salt.

14. A process as in claim 6, wherein the synthetic anion resin has a specific surface area of 5 m²/g-dry resin or more.

15. A process as in claim 6, wherein the total volume of macropores with pore sizes from 100 Å to 2,000 Å in the synthetic resin is 0.2 c/g or more.

16. A process as in claim 6, wherein the average pore size of the pores in the synthetic resin is from about 150 Å to about 1,000 Å.

17. A process as in claim 7, wherein anion exchange capacity on the basis of primary, secondary and/or tertiary amino group excluding diethylaminoethyl groups is at least 1 meq/g-dry resin.

18. The enzyme-immobilization carrier according to claim 1, wherein the synthetic anion-exchange resin comprises a phenol-formaldehyde condensate matrix having primary amino groups, secondary amino groups and a mixture thereof and diethylaminoethyl groups linked to the matrix through an ether linkage or to said primary or secondary amino group to form a secondary or tertiary amino group respectively, the ion-exchange capacity provided by the diethylaminoethyl groups is not less than 1 meq/g-dry resin, and the total ion-exchange capacity of the resin is not less than 2 meq/g-dry resin.

19. The enzyme-immobilization carrier according to claim 1, wherein the synthetic anion-exchange resin comprises a phenol-formaldehyde condensate matrix and diethylaminoethyl groups linked to the matrix through an ether linkage and the ion-exchange capacity of the resin is not less than 2 meq/g-dry resin.

20. The enzyme-immobilization carrier according to claim 1, wherein the synthetic anion-exchange resin comprises a crosslinked polystyrene matric having primary amino groups, secondary amino groups or a mixture thereof and diethylaminoethyl groups linked to said primary or secondary amino group to form a secondary or tertiary amino group respectively, the ion-exchange capacity provided by the diethylaminoethyl groups is not less than 1 meq/g-dry resin and the total ion-exchange capacity of the resin is not less than 2 meq/g-dry resin.

21. The enzyme-immobilization carrier according to claim 18, wherein the ion-exchange capacity provided by the diethylaminoethyl groups is not less than 1.5 meq/g-dry resin.

22. The enzyme-immobilization carrier according to claim 18, wherein the ion-exchange capacity provided by the diethylamineothyl groups is not less than 1.5 meq/g-dry resin.

* * * * *